United States Patent [19]
Nedelec et al.

[11] 4,189,477
[45] Feb. 19, 1980

[54] NOVEL Δ⁴-PREGNENES
[75] Inventors: Lucien Nedelec, Le Raincy; André Pierdet, Noisy-le-Sec; Roger Deraedt, Les Pavillons-sous-Bois, all of France
[73] Assignee: Roussel Uclaf, Paris, France
[21] Appl. No.: 903,600
[22] Filed: May 8, 1978
[30] Foreign Application Priority Data
   May 6, 1977 [FR] France .................................. 77 13864
[51] Int. Cl.² .......................... A61K 31/56; C07J 1/00
[52] U.S. Cl. .................................. 424/243; 260/397.45
[58] Field of Search ................... 260/397.45; 424/243; /Steroids MS File Primary Examiner—Elbert L. Roberts
Attorney, Agent, or Firm—Hammond & Littell

[57] ABSTRACT

Novel Δ⁴-pregnenes of the formula

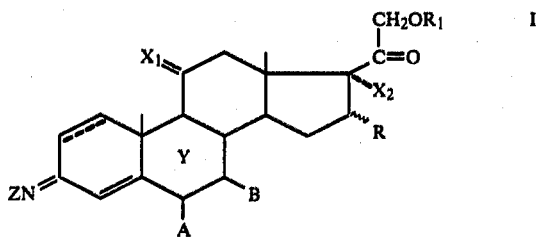

wherein $X_1$ is selected from the group consisting of =O and

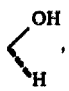

Y is selected from the group consisting of hydrogen and halogen, $R_1$ is selected from the group consisting of hydrogen and acyl of an organic carboxylic acid of 1 to 18 carbon atoms, $X_2$ is selected from the group consisting of hydrogen and —OH, R in the 16α- or β-position is selected from the group consisting of hydrogen, —OH and methyl, Z is selected from the group consisting of (1) —OH, (2) alkoxy of 1 to 12 carbon atoms, (3) cycloalkoxy of 3 to 12 carbon atoms, (4) acyloxy of an organic carboxylic acid of 1 to 18 carbon atoms, (5)

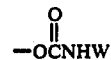

wherein W is a hydrocarbon of 1 to 12 carbon atoms, (6)

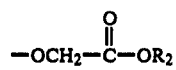

wherein $R_2$ is hydrogen or alkyl of 1 to 12 carbon atoms, (7)

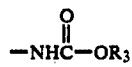

wherein $R_3$ is a hydrocarbon of 1 to 12 carbon atoms and (8)

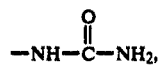

the dotted line in the A ring indicates the optional presence of a double bond in the 1(2)-position and A and B are both hydrogen or A is methyl, chlorine or fluorine while B is hydrogen or A and B may form a double bond in the 6(7)-position with the proviso that if the A ring has a 1(2) double bond, A is hydrogen or fluorine, B is hydrogen, Y is hydrogen or fluorine, $X_2$ is hydrogen or —OH, R is methyl and Z is not —OH having a very marked antiallergic activity with a reduced anti-inflammatory activity and a process for their preparation.

23 Claims, No Drawings

NOVEL Δ⁴-PREGNENES

STATE OF THE ART

Steroids containing an oxime group in the 3-position are described in U.S. Pat. No. 3,074,979, French Patent No. 1,600,937 and German Patent No. 1,568,520.

OBJECTS OF THE INVENTION

It is an object of the invention to provide the novel Δ⁴-pregnenes of formula I and to provide a novel process for their preparation.

It is another object of the invention to provide novel antiallergic compositions and to a novel method of treating or preventing allergic reactions in warm-blooded animals.

These and other objects and advantages of the invention will become obvious from the following detailed description.

THE INVENTION

The novel Δ⁴-pregnenes of the invention have the formula

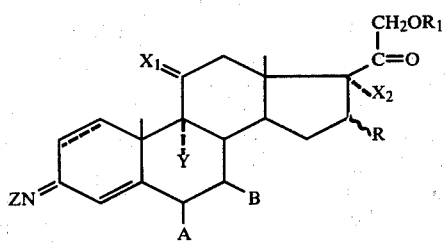

wherein $X_1$ is selected from the group consisting of $=O$ and

Y is selected from the group consisting of hydrogen and halogen, $R_1$ is selected from the group consisting of hydrogen and acyl of an organic carboxylic acid of 1 to 18 carbon atoms, $X_2$ is selected from the group consisting of hydrogen and —OH, R in the 16α- or β-position is selected from the group consisting of hydrogen, —OH and methyl, Z is selected from the group consisting of (1) —OH, (2) alkoxy of 1 to 12 carbon atoms, (3) cycloalkoxy of 3 to 12 carbon atoms, (4) acyloxy of an organic carboxylic acid of 1 to 18 carbon atoms, (5)

wherein W is a hydrocarbon of 1 to 12 carbon atoms, (6)

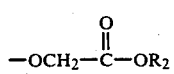

wherein $R_2$ is hydrogen or alkyl of 1 to 12 carbon atoms, (7)

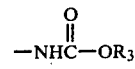

wherein $R_3$ is a hydrocarbon of 1 to 12 carbon atoms and (8)

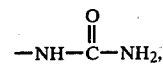

the dotted line in the A ring indicates the optional presence of a double bond in the 1(2)-position and A and B are both hydrogen or A is methyl, chlorine or fluorine while B is hydrogen or A and B may form a double bond in the 6(7)-position with the proviso that if the A ring has a 1(2) double bond, A is hydrogen or fluorine, B is hydrogen, Y is hydrogen or fluorine, $X_2$ is hydrogen or —OH, R is methyl and Z is not —OH.

Among the preferred compounds of formula I are those where Z is not —OH or alkoxy and $X_2$ is —OH, R and Y are hydrogen and A and B are both hydrogen.

The compounds of formula I can exist in the syn and anti diastereoisomeric forms due to the existence of the C=N double bond and the invention is directed to the syn isomers, anti isomers and mixtures of the syn and anti isomers which can be separated by conventional methods such as crystallization of chromatography.

Examples of $R_1$ as an acyl of an organic carboxylic acid of 1 to 18 carbon atoms are saturated or unsaturated aliphatic and cycloaliphatic carboxylic acids and especially alkanoic acids such as acetic acid, formic acid, propionic acid, butyric acid, isobutyric acid or undecylic acid and cycloalkylcarboxylic acids and cycloalkylalkanoic acids such as cyclopropylcarboxylic acid, cyclopentylcarboxylic acid, cyclohexylcarboxylic acid, cyclopropylacetic acid, cyclopropylpropionic acid, cyclopentylacetic acid, cyclopentylpropionic acid, cyclohexylacetic acid or cyclohexylpropionic acid; benzoic acid; phenylalkanoic acids such as phenylacetic acid or phenylpropionic acid; amino acids such as diethylaminoacetic acid or aspartic acid.

Examples of Z when it is alkoxy are methoxy, ethoxy, propoxy, isopropoxy, butoxy, isobutoxy, tert.-butoxy, n-pentyloxy, n-hexyloxy, 2-methyl-pentyloxy, 2,3-dimethylbutoxy, n-heptyloxy, 2-methyl-hexyloxy, 2,2-dimethyl-pentyloxy, 3,3-dimethyl-pentyloxy, 3-ethyl-pentyloxy, n-octyloxy, 2,2-dimethylhexyloxy, 3,3-dimethyl-hexyloxy, 3-methyl-3-ethylpentyloxy, nonyloxy, 2,4-dimethyl-heptyloxy and n-decyloxy.

Examples of Z when it is cycloalkyloxy are cyclopentyloxy and cyclohexyloxy and when Z is acyloxy, the acids may be of the type described above with respect to $R_1$. When Z is aminocarbonyloxy, it is preferably

when W is alkyl, aryl or aralkyl. Examples of W are alkyl of 1 to 12 carbon atoms as discussed above for Z and aryl or aralkyl such as phenyl or benzyl optionally substituted in the ortho, meta or para positions with at least one member of the group consisting of alkyl of 1 to 4 carbon atoms such as methyl, halogens such as chlorine, fluorine and —$CF_3$.

When Z is —OCH$_2$—COOR$_2$, R$_2$ is either hydrogen or an alkyl of 1 to 12 carbon atoms as discussed above for Z. When Z is —NH—COOR$_3$, R$_3$ is preferably alkyl as discussed above for Z.

The compounds of the invention may be saturated or unsaturated in the 1(2) position. Among the preferred compounds of formula I are those wherein A and B are hydrogen, those wherein X$_1$ is

those wherein X$_2$ is —OH or hydrogen, those wherein R is 16α-methyl, those wherein Y is 9α-fluoro, those wherein R$_1$ is hydrogen and those wherein R$_1$ is acyl of an organic carboxylic acid of 1 to 18 carbon atoms. The most preferred compounds are the syn and anti isomers of 3-methoxyimino-9α-fluoro-16α-methyl-Δ$^4$-pregnene-11β,17α,21-triol-20-one.

The novel process of the invention for the preparation of compounds of formula I comprises reacting a compound of the formula

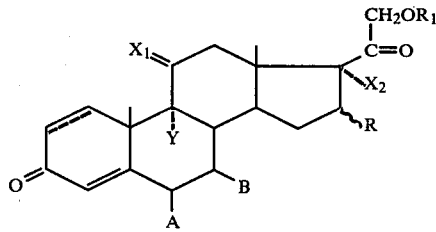

wherein the dotted lines and the substituents have the above definitions with a compound of the formula

    III or an acid addition salt thereof wherein Z' is selected from the group consisting of —OH, alkoxy of 1 to 12 carbon atoms, cycloalkyloxy of 3 to 12 carbon atoms, —OCH$_2$—COOR$_2$ or —NHCOOR$_3$ or

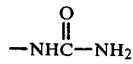

wherein R$_2$ and R$_3$ have the above definitions to obtain a compound of the formula

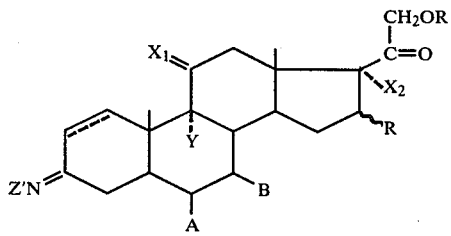

and if Z' is —OH, the latter may be reacted with an esterification agent to obtain a compound of formula I wherein Z is acyloxy or may be reacted with a compound of the formula W-N=C=O to obtain a compound of formula I wherein Z is

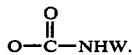

The syn and anti isomers may be separated by chromatography, crystallization or any other known methods.

In a preferred mode of the process, the compound of formula III is used in the form of an acid addition salt such as the hydrochloride and the esterification agent is the acid anhydride. The reactions may be effected at room temperature or below.

Compounds of formula I in which R$_1$ is an acyl of an organic carboxylic acid of 1 to 18 carbon atoms may be saponified with a saponification agent such as sodium hydroxide or potassium hydroxide to obtain the corresponding compound of formula I wherein R$_1$ is hydrogen. Compounds of formula IA wherein Z' is —OCH$_2$—COOR$_2$ in which R$_2$ is alkyl of 1 to 12 carbon atoms may also be saponified with a saponification agent such as sodium hydroxide or potassium hydroxide to form the corresponding compound of formula I wherein Z is —OCH$_2$—COOH.

The novel antiallergic compositions of the invention are comprised of an antiallergically effective amount of at least one compound of formula I and an inert pharmaceutical carrier or excipient. The compositions may be in the form of tablets, coated tablets, dragees, gelules, granules, suppositories, injectable solution or suspension, pomades, creames, gels and aerosol preparations prepared in known manner.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, preservatives and diverse wetting agents, dispersants and emulsifiers.

The compositions have a very marked antiallergic activity, comparable or superior to that of dexamethasone but has less anti-inflammatory activity than dexamethasone. This dissociation of antiallergic and antiinflammatory activities is of a great interest as it is possible to use the compounds of formula I at doses where only the antiallergic activity is manifested without classical secondary side effects of anti-inflammatory steroids.

The compositions of the invention are useful for the treatment of seasonal or not periodic rhinitsis, asthma and cutaneous troubles of diverse origins such as urticairy. The preferred compositions contain the anti or syn isomers of 3-methoxyimino-9α-fluoro-16α-methyl-Δ$^4$-pregnene-11β,17α,21-triol-20-One.

The novel method of treating allergic conditions in warm-blooded animals, including humans, comprises administering to warm-blooded animals an antiallergically effective amount of at least one compound of formula I. The compounds may be administered orally, rectally, parenterally or topically to the skin or mucus, preferably orally. The usual effective dose is 0.01 to 2 mg/kg depending on the complaint treated, the specific compound and the method of administration.

In the following examples there are described several preferred embodiments to illustrate the invention. However, it should be understood that the invention is not intended to be limited to the specific embodiments.

EXAMPLE 1 syn and anti isomers of
3-hydroxyimino-9α-fluoro-16α-methyl-21-acetyloxy-
Δ$^4$-pregnene-11β,17α-diol-20-one A suspension of 5 g of 9α-fluoro-16α-methyl-21-acetyloxy-Δ$^4$-pregnene-11β,17α-diol-3,20-dione [prepared as in J.A.C.S., Vol. 80 (1958), p. 3161], 1 g of hydroxylamine hydrochloride and 50 ml of ethanol was stirred for 20 hours at room temperature and the ethanol was evaporated. The residue was chromatographed over silica gel and was eluted with an 8-2 chloroform-acetone mixture. First recovered were 2.6 g of a product with a Rf=0.3 which was empasted in hot isopropyl ether to obtain 2 g of the anti isomer of 3-hydroxyimino-9α-fluoro-16α-methyl-21-acetyloxy-Δ$^4$-pregnene-11β,17α-diol-20-one melting at 210° C.

RMN Spectrum (CDCl$_3$ 60 MHz):

85.5 Hz (19-methyl); 60.5 Hz (18-methyl); 50.5–58 Hz (16α-methyl); 351 Hz (ethylenic 4-hydrogen); 255–264 Hz (11-hydrogen).

A second yield was 1.9 g of a product with an Rf=0.15 which was empasted with hot isopropyl ether to obtain 1.4 g of the syn isomer of the said product melting at 210° C.

RMN Spectrum (CDCl$_3$—60 MHz):

86.5 Hz (19-methyl); 60.5 Hz (18-methyl); 50–57 Hz (16α-methyl); 255–265 Hz (11-hydrogen); 390 Hz (ethylenic 4-hydrogen).

EXAMPLE 2 syn and anti isomers of
3-methoxyimino-9α-fluoro-16α-methyl-Δ$^4$-pregnene-
11β,17α,21-triol-20-one A solution of 6.4 g of 9α-fluoro-16α-methyl-Δ$^4$-pregnene-11β,17α,21-triol-3,20-dione and 1.760 g of 0-methyl-hydroxylamine hydrochloride in 510 ml of methanol was stirred for 2 hours and was then diluted with water. The mixture was extracted with ethyl acetate and the extracts were evaporated to dryness. The 7.2 g of raw residue was chromatographed over silica gel and was eluted with an 8-2 benzene-ethyl acetate mixture to obtain a first yield of 3.2 g of a product with an Rf=0.35 which after crystallization from methyl ethyl ketone yielded 2.130 g of the anti isomer of 3-methoxyimino-9α-fluoro-16α-methyl-Δ$^4$-pregnene-11β,17α, 21-triol-20-one melting at 254° C. and having a specific rotation of $[\alpha]_D^{20} = +164° \pm 3.5°$ (c=0.6% in ethanol) and a second yield of 2.6 g of product with an Rf=0.21 which after crystallization from aqueous ethanol yielded 1.875 g of the syn isomer of 3-methoxyimino-9α-fluoro-16α-methyl-Δ$^4$-pregnene-11β,17α, 21-triol-20-one melting at 246° C. and having a specific rotation of $[\alpha]_D^{20} = +214.5° \pm 3°$ (c=0.5% in ethanol).

EXAMPLE 3 anti and syn isomers of
3-methoxyimino-9α-fluoro-16α-methyl-Δ$^{1,4}$-pregnadiene-11β,17α, 21-triol-20-one 1.640 g of 0-methyl hydroxylamine dihydrochloride was added to a solution of 5 g of 9α-fluoro-16α-methyl-Δ$^{1,4}$-pregnadiene-11β,17α, 21-triol-3,20-dione in 300 ml of methanol and the resulting suspension was stirred at 22°–23° C. for 6 hours. 15.3 ml of N sodium hydroxide were added to the mixture which was concentrated to 100 ml under reduced pressure at 40° C. Then, 800 ml of distilled water were slowly added thereto and the mixture was filtered. The product was dried under reduced pressure to obtain 5.083 g of raw product which was chromatographed over silica gel. Elution with a 7-3 benzene-ethyl acetate mixture yielded 2.487 g of the anti isomer of 3-methoxyimino-9α-fluoro-16α-methyl-Δ$^{1,4}$-pregnadiene-11β,17α, 21-triol-20-one which after crystallization from dimethoxypropane melted at 196° C. and had a specific rotation of $[\alpha]_D^{20} = +109.5°$ (c=0.58% in ethanol) and a second yield of 1.802 g of the syn isomer of the said product which after crystallization from dimethoxy propane melted at 198° C. and had a specific rotation of $[\alpha]_D^{20} = +135°$ (c=0.54% in ethanol).

EXAMPLE 4 anti and syn isomers of
3-methoxyimino-9α-fluoro-16α-methyl-Δ$^4$-pregnene-
11β,21-diol-20-one A solution of 12 g of 9α-fluoro-16α-methyl-Δ$^4$-pregnene-11β,21-diol-3,20-dione [process of British patent No. 935,611], 3.7 g of 0-methyl-hydroxylamine hydrochloride and 600 ml of methanol was stirred for 2 hours at room temperature and was then filtered. The recovered product was washed and dried to obtain 5.350 g of raw product which was crystallized from methyl ethyl ketone to obtain 3.090 g of the anti isomer of 3-methoxyimino-9α-fluoro-16α-methyl-Δ$^4$-pregnene-11β,21-diol-20-one with an Rf=0.41, a melting point of 262° C. and a specific rotation of $[\alpha]_D^{20} = +201° \pm 3°$ (c=0.1% in chloroform).

The filtrate was concentrated to about 100 ml and was poured into 100 ml of ice water. The mixture was vacuum filtered and the recovered product was dried and chromatographed over silica gel. Elution with a 98-2 chlororform-methanol mixture yielded 3 g of the anti isomer with an Rf=0.41 and 3.14 g of the said product with an Rf=0.30 which after crystallization from isopropanol yielded 1.536 g of the syn isomer melting at 212° C. and having a specific rotation of $[\alpha]_D^{20} = +252° \pm 4°$ (c=0.7% in chloroform).

EXAMPLE 5 anti and syn isomers of
3-ethoxyimino-9α-fluoro-16α-methyl-Δ$^4$-pregnene-
11β,17α,21-triol-20-one A suspension of 12 g of 9α-fluoro-16α-methyl-Δ$^4$-pregnene-11β,17α,21-triol-3,20-dione, 3.540 g of O-ethyl-hydroxylamine hydrochloride and 960 ml of methanol was reacted for 15 minutes and the resulting solution was stirred at room temperature for 4 hours. The mixture was poured into ice water and the mixture was vacuum filtered. The recovered product was washed and dried to obtain 12.8 g of product which was chromatographed over silica gel. Elution with a 7-3 benzene-ethyl acetate mixture yielded 6 g of a product with an Rf=0.42 which was crystallized from isopropanol to obtain 2.720 g of the anti isomer of 3-ethoxyimino-9α-fluoro-16α-methyl-Δ$^4$-pregnene-11β,17α,21-triol-20-one melting at 200° C. and having a specific rotation of $[\alpha]_D^{20} = +171° \pm 3.5°$ (c=0.57% in ethanol) and a second part of 5 g of product with an Rf=0.27 which was crystallized from dimethoxypropane to obtain 1.5 g of the syn isomer melting at 192° C. and having a specific rotation of $[\alpha]_D^{20} = +228° \pm 4.5°$ (c=0.5% in ethanol).

EXAMPLE 6 syn and anti isomers of 3-acetyloxyimino-9α-fluoro-16α-methyl-21-acetyloxy-Δ⁴-pregnene-11β,17α-diol-20-one A suspension of 8.2 g of 9α-fluoro-16α-methyl-21-acetyloxy-Δ⁴-pregnene-11β,17α-diol-3,20-dione, 1.7 g of hydroxylamine hydrochloride and 80 ml of ethanol was stirred at room temperature for 20 hours and the ethanol was evaporated. The residue was taken up in isopropyl ether and the mixture was filtered. The crystals were dried to obtain 10.3 g of product which was dissolved in 40 ml of pyridine and 20 ml of acetic acid anhydride. The mixture was heated at 60° C. for 1 hour and the solution was poured into an ice-water mixture. The mixture was filtered and the crystals were washed and dried to obtain 9.7 g of product which chromatographed over silica gel. Elution with a 9–1 chloroform-acetone mixture yielded 4.2 g of product with an Rf=0.50 which was crystallized from acetone to obtain 3.4 g of the anti isomer of 3-acetyloxyimino-9α-fluoro-16α-methyl-21-acetyloxy-Δ⁴-pregnene-11β,17α-diol-20-one melting at 260° C.

RMN Spectrum (CDCl$_3$ – 60 MHz):
362 Hz (ethylenic 4-H); 254–264 Hz (11-hydrogen); 61 Hz (18-methyl); 86 Hz (19-methyl); 51–58 Hz (16α-methyl).

A second yield of 4.5 g of product with an Rf=0.30 was obtained which was crystallized from acetone to obtain 3.3 g of the syn isomer melting at 140° C.

RMN Spectrum (CDCl$_3$ – 60 MHz):
386 Hz (ethylenic 4H); 254–264 Hz (11-hydrogen); 60.5 Hz (18-methyl); 87.5 Hz (19-methyl); 51–58 Hz (16α-methyl).

EXAMPLE 7 anti and syn isomers of 3-methoxyimino-9α-fluoro-16α-methyl-21-acetyloxy-Δ⁴-pregnene-11β-ol-20-one 4.010 g of O-methyl-hydroxylamine hydrochloride were added at 45° C. to a solution of 14.350 g of 9α-fluoro-16α-methyl-21-acetyloxy-Δ⁴-pregnene-11β-ol-3,20-dione in 1150 ml of methanol and the reaction mixture was stirred for 25 minutes and was then concentrated to 150 ml. The mixture was poured into ice water and was vacuum filtered. The recovered product was washed and dried to obtain 14.840 g of product which was chromatographed over silca gel. Elution with a 95–5 chloroform-acetone mixture to obtain 6.60 g of product with an Rf=0.31 which was crystallized from isopropanol to obtain 5.800 g of the anti isomer of 3-methoxyimino-9α-fluoro-16α-methyl-21-acetyloxy-Δ⁴-pregnene-11β-ol-20-one melting at 252° C. and having a specific rotation of $[\alpha]_D^{20} = +205° \pm 3°$ (c=0.7% in ethanol) and a second yield of 3.90 g of product with an Rf=0.15 which was crystallized from isopropanol to obtain 3.260 g of the syn isomer with a specific rotation of $[\alpha]_D^{20} = +258° \pm 4°$ (c=0.5% in ethanol).

EXAMPLE 8 syn and anti isomers of methyl 2-[(9α-fluoro-16α-methyl-Δ⁴-pregnene-11β,17α,21-triol-20-one-3-ylidene)-aminooxy]-acetate 5 g of 9α-fluoro-16α-methyl-Δ⁴-pregnene-11β,17α,21-triol-3,20-dione and 1.66 g of aminooxyacetic acid hemihydrochloride were suspended in 200 ml of methanol and the product slowly dissolved and the resulting solution was stirred at 22°–23° C. for 19 hours. The mixture was evaporated to dryness and the residue was taken up in 200 ml of water and 20 ml of a saturated aqueous sodium bicarbonate solution. The mixture was vacuum filtered and the product was washed and dried to obtain 6 g of product which was chromatographed over silica gel. Elution with a 1—1 benzene-ethyl acetate mixture yielded 2.0 g of product with an Rf=0.23 which was crystallized from dimethoxypropane to obtain the anti isomer of methyl 2-[(9α-fluoro-16α-methyl-Δ⁴-pregnene-11β,17α,21-triol-20-one-3-ylidene)-aminooxy]-acetate melting at 173° C. and having a specific rotation of $[\alpha]_D^{20} = +39° \pm 2.5°$ (c=1% in ethanol) and a second product of 1.857 g of a product with an Rf=0.19 which was chromatographed over silica gel and crystallized from dimethoxypropane and isopropanol to obtain the syn isomer melting at 208° C. and having a specific rotation of $[\alpha]_D^{20} = +212° \pm 4°$ (c=0.4% in ethanol).

EXAMPLE 9 syn isomer of 2-[(9α-fluoro-16α-methyl-Δ⁴-pregnene-11β,17α,21-triol-20-one-3-ylidene)-aminooxy]-acetic acid 11.7 ml of N sodium hydroxide solution were added with stirring to a suspension of 3.78 g of the syn isomer of Example 8 in 38 ml of ethanol and the mixture was stirred at 22° C. for 10 minutes and was then cooled in an ice bath. 400 ml of distilled water and 11.7 ml of N hydrochloric acid were added to the reaction mixture which was then filtered. The recovered product was washed and dried to obtain 2.911 g of product which was dissolved in 100 ml of dioxane. The solution was filtered to remove insoluble and the filtrate was evaporated to dryness. The residue was crystallized from 10 ml of ethyl acetate to which 3 ml of isopropyl ether were added dropwise. The mixture was vacuum filtered and the product was washed by empasting with iced ethyl acetate. The resulting crystals were empasted with isopropyl ether and were dried under reduced pressure to obtain 2.124 g of the syn isomer of 2-[(9α-fluoro-16α-methyl-Δ⁴-pregnene-11β,17α,21-triol-20-one-3-ylidene)-aminooxy]acetic acid melting at 236° C. and having a specific rotation of $[\alpha]_D^{20} = +207° \pm 4°$ (c=0.5% in ethanol).

EXAMPLE 10 anti isomer of 2-[(9α-fluoro-16α-methyl-Δ⁴-pregnene-11β,17α,21-triol-20-one-3-ylidene)-aminooxy]-acetic acid 14.5 ml of N sodium hydroxide solution were slowly added to a suspension of 4.650 g of the anti isomer of Example 8 in 47 ml of ethanol and the mixture was stirred at 20° C. for 10 minutes and was then diluted with ice water. 14.5 ml of N hydrochloric acid were added to the mixture which was then filtered. The recovered product was washed with water and dried to obtain 3.477 g of product which was crystallized from dimethoxypropane to obtain 1.976 g of the anti isomer of 2-[(9α-fluoro-16α-methyl-Δ⁴-pregnene-11β,17α,21-triol-20-one-3-ylidene)-aminooxy]-acetic acid melting at 211° C. and having a specific rotation of $[\alpha]_D^{20} = +151° \pm 3°$ (c=0.47% in ethanol).

EXAMPLE 11 syn and anti isomers of 3-methoxyimino-16α-methyl-21-aceyloxy-Δ⁴-pregnene-11β,17α-diol-20-one A suspension of 10.2 g of 16α-methyl-21-acetyloxy-Δ⁴-pregnene-11β,17α-diol-3,20-dione [Belgium patent No. 564,914], 2.2 g of O-methyl-hydroxylamine hydrochloride and 800 ml of methanol was stirred for 5 hours at room temperature and the reaction mixture was poured into an icewater mixture. The mixture was filtered and the crystals were washed with water and dried to obtain 8.6 g of a first crop. The wash waters were extracted with ethyl acetate and the organic extracts were evaporated to dryness under reduced pressure at 40° C. to obtain a second crop of 2 g of product. The combined products were chromatographed over silica gel and elution with a 7-3 benzene-ethyl acetate mixture yielded 4.6 g of product with a Rf=0.70 which was the anti isomer of 3-methoxyimino-16α-methyl-21-acetyloxy-Δ⁴-pregnene-11β,17α-diol-20-one melting at 185° C. with an RMN Spectrum (CDCl₃): 5.69 ppm (ethylenic 4-hydrogen) and 3.2 g of the syn isomer of 3-methoxyimino-16α-methyl-21-acetyloxy-Δ⁴-pregnene-11β,17α-diol-20-one with an Rf=0.40 and melting at 182° C. RMN Spectrum (CDCl₃): 6.33 ppm (ethylenic 4-hydrogen).

EXAMPLE 12 anti isomer of 3-methoxyimino-16α-methyl-Δ⁴-pregnene-11β,17α,21-triol-20-one

A solution of 4.2 g of the anti isomer of Example 1, 4 ml of 1 N methanolic potassium hydroxide and 60 ml of methanol was stirred for 30 minutes at 20°-25° C. and was then poured into water. The mixture was filtered and the crystals were washed and dried to obtain 3 g of product which was crystallized from ethyl acetate to obtain 2.9 g of the anti isomer of 3-methoxyimino-16α-methyl-Δ⁴-pregnene-11β,17α,21-triol-20-one melting at 220°-222° C. and having a specific rotation of $[\alpha]_D^{20} = +168° \pm 3.5°$ (c=1.0% in chloroform). RMN Spectrum (CDCl₃): 5.73 ppm (ethylenic 4-hydrogen).

EXAMPLE 13 syn isomer of 3-methoxyimino-16α-methyl-Δ⁴-pregnene-11β,17α,21-triol-20-one

A solution of 2.9 g of the syn isomer of Example 1, 45 ml of methanol and 3 ml of 1 N methanolic potassium hydroxide stood for 30 minutes at 20°-25° C. and was then poured into a water-ice mixture to obtain a milky solution. The mixture was extracted with ethyl acetate and the extracts were evaporated to dryness under reduced pressure at 40° C. The residue was empasted with isopropyl ether, was filtered and dried to obtain 2.1 g of product which was crystallized from refluxing isopropyl ether to obtain 1.9 g of the syn isomer of 3-methoxyimino-16α-methyl-Δ⁴-pregnene-11β,17α,21-triol-20-one melting at 167° C. and having a specific rotation of $[\alpha]_D^{20} = +228° \pm 4°$ (c=0.8% in CHCl₃).

EXAMPLE 14 syn and anti isomer of 3-methoxyimino-9α-fluoro-16α-methyl-21-acetyloxy-Δ⁴-pregnene-11β,17α-diol-20-one A solution of 15 g of 9α-fluoro-16α-methyl-21-acetyloxy-Δ⁴-pregnene-11β,17α-diol-3,20-dione, 4.040 g of O-methyl-hydroxylamine hydrochloride and 1200 ml of methanol was stirred for 3 hours at 20° C. and was then concentrated to 300 ml and was poured into ice water. The mixture was stirred for 30 minutes and was vacuum filtered. The crystals were washed with aqueous sodium bicarbonate solution, then with water, dried under reduced pressure over phosphoric anhydride to obtain 15.2 g of product which was chromatographed over silica gel. Elution with a 9-1 chloroform-acetone mixture yielded 6.05 g of a product with an Rf=0.34 which was crystallized from isopropanol and then dimethoxypropane to obtain 3.73 g of the anti isomer of 3-methoxyimino-9α-fluoro-16α-methyl-21-acetyloxy-Δ⁴-pregnene-11β,17α-diol-20-one melting at 198° C. and having a specific rotation of $[\alpha]_D^{20} = 172° \pm 3°$ (c=0.6% in ethanol) and 4.20 g of a product with an Rf=0.17 which was crystallized from isopropanol to obtain 3.760 g of the syn isomer melting at 218° C. and having a specific rotation of $[\alpha]_D^{20} = +219° \pm 4°$ (c=0.5% in ethanol).

RMN Spectrum (CDCl₃):
anti isomer 5.82 ppm (ethylenic 4-hydrogen)
syn isomer 6.43 ppm (ethylenic 4-hydrogen)

EXAMPLE 15 syn and anti isomer of 3-methoxyimino-9α-fluoro-16α-methyl-21-acetyloxy-Δ¹,⁴-pregnadiene-11β,17α-diol-20-one A solution of 15 g of 9α-fluoro-16α-methyl-21-acetyloxy-Δ¹,⁴-pregnadiene-11β,17α-diol-3,20-dione, 4.433 g of O-methyl-hydroxylamine hydrochloride and 900 ml of methanol was stirred for 5 hours at 22° C. and 41 ml of a N sodium hydroxide solution were added thereto. The mixture was concentrated to 100 ml at 40° C. and 1000 ml of distilled water were added thereto. The mixture was iced and vacuum filtered and the crystals were washed with water and dried to obtain 16.530 g of a product which was chromatographed over silica gel. Elution with a 9-1 chloroform-acetone mixture yielded 6.1 g of a product with an Rf=0.35 and melting at 262° C. which was crystallized from isopropanol and then methyl ethyl ketone to obtain the anti isomer of 3-methoxyimino-9α-fluoro-16α-methyl-21-acetyloxy-Δ¹,⁴-pregnadiene-11β,17α-diol-20-one melting at 264° C. and having a specific rotation of $[\alpha]_D^{20} = +117° \pm 3°$ (c=0.54% in pyridine) and 5.6 g of a product with an Rf=0.2 which was crystallized from 2,2-dimethoxypropane to obtain the syn isomer with a melting point of 193° C. and a specific rotation of $[\alpha]_D^{20} = +143° \pm 2.5°$ (c=1% in ethanol).

RMN Spectrum (CDCl₃):
anti isomer—6.02 ppm (ethylenic-4-hydrogen)
syn isomer—6.683 ppm (ethylenic-4-hydrogen)

EXAMPLE 16 syn and anti isomer of 3-cyclopentyloxyimino-9α-fluoro-16α-methyl-Δ⁴-pregnene-11β,17α,21-triol-20-one A solution of 10 g of 9α-fluoro-16α-methyl-Δ⁴-pregnene-11β,17α,21-triol-3,20-dione, 3.820 g of O-cyclopentyl-hydroxylamine hydrochloride and 600 ml of methanol was stirred for 15 hours and 27.8 ml of a N sodium hydroxide solution were added thereto. The mixture was concentrated to 100 ml and was diluted with water and was vacuum filtered. The crystals were washed with water and dried to obtain 11.9 g of a product which was chromatographed over silica gel. Elution with a 7-3 benzene-ethyl acetate mixture yielded 5.8 g of a product with an Rf=0.33 which was crystallized from methyl ethyl ketone and then ethyl acetate to obtain the anti isomer of 3-cyclopentyloxyimino-9α-fluoro-16α-methyl-Δ⁴-pregnene-11β,17α,21-triol-20-one melting at 228° C. and having a specific rotation of $[\alpha]_D^{20} = +159.5° \pm 3.5°$ (c=0.6% in ethanol) and 4.6 g of a product with an Rf=0.17 which was crystallized from dimethoxypropane and then from an isopropyl ether-methylene chloride mixture to obtain the syn isomer with a melting point of 212° C. and a specific rotation of $[\alpha]_D^{20} = +228° \pm 3.5°$ (c=0.5% in ethanol).

RMN Spectrum (CDCl₃):
anti isomer 5.86 ppm (ethylenic 4-hydrogen)
syn isomer 6.42 ppm (ethylenic 4-hydrogen)

EXAMPLE 17 syn and anti isomers of 3-(2-ethoxycarbonylhydrazone) of 9α-fluoro-16α-methyl-Δ¹,⁴-pregnadiene-11β,17α,21-triol-3,20-dione 76 ml of 2 N hydrochloric acid and 15 g of 9α-fluoro-16α-methyl-Δ¹,⁴-pregnadiene-11β,17α,21-triol-3,20-dione were added under nitrogen with stirring to a solution of 15.9 g of ethyl carbazate in 1050 ml of ethanol and the mixture was stirred for 48 hours at room temperature. 152 ml of N sodium hydroxide solution were added thereto and the ethanol was distilled off and 1000 ml of water were added. The mixture was vacuum filtered and the crystals were washed and dried to obtain 18.6 g of product which was chromatographed over silica gel. Elution with a 2-8 benzene-ethyl acetate mixture yielded 5.210 g of a product with an Rf=0.3 which solidified in dimethoxypropane to obtain the anti isomer of the 3-(2-ethoxycarbonylhydrazone) of 9α-fluoro-16α-methyl-Δ¹,⁴-pregnadiene-11β,17α,21-triol-3,20-dione melting at 190° C. and having a specific rotation of $[\alpha]_D^{20} = +94.5° \pm 2°$ (c=0.9% in ethanol) and 5.630 g of a product with an Rf=0.25 which was crystallized from isopropanol and then methyl ethyl ketone to obtain the syn isomer melting at 300° C. and with a specific rotation of $[\alpha]_D^{20} = +148.5° \pm 3.5°$ (c=0.5% in ethanol).

RMN Spectrum
anti isomer (CDCl₃): 6.18 ppm (ethylenic 4-hydrogen)
syn isomer (DMSO): 6.7 ppm (ethylenic 4-hydrogen)

EXAMPLE 18 syn and anti isomers of semicarbazone of 9α-fluoro-16α-methyl-Δ¹,⁴-pregnadiene-11β,17α,21-triol-3,20-dione A solution of 10 g of 9α-fluoro-16α-methyl-Δ¹,⁴-pregnadiene-11β,17α,21-triol-3,20-dione, 3.412 g of semicarbazide hydrochloride and 600 ml of methanol were stirred under nitrogen for 16 hours at 20°-22° C. and 30.6 ml of a N sodium hydroxide solution were added thereto. The mixture was evaporated to dryness under reduced pressure at 40° C. and the residue was empasted with water and vacuum filtered. The product was washed and dried to obtain 10.6 g of a product which was chromatographed over silica gel. Elution with a 9-1 chloroform-methanol mixture yielded 5.3 g of a product with an Rf=0.18 which was empasted with dimethoxypropane to obtain the syn isomer of the semicarbazone of 9α-fluoro-16α-methyl-Δ¹,⁴-pregnadiene-11β,17α,21-triol-3,20-dione melting at 300° C. and having a specific rotation of $[\alpha]_D^{20} = +206° \pm 4°$ (c=0.5% in ethanol) and 3.8 g of a product with an Rf=0.12 which was crystallized from isopropanol and then methyl ethyl ketone to obtain the anti isomer with a specific rotation of $[\alpha]_D^{20} = +78.5° \pm 2.5°$ (c=0.6% in ethanol).

RMN Spectrum (DMSO):
anti isomer: 5.93 ppm (ethylenic 4-hydrogen)
syn isomer: 6.75 ppm (ethylenic 4-hydrogen)

EXAMPLE 19 syn and anti isomers of 3-(phenylaminocarbonyloxyimino)-9α-fluoro-16α-methyl-21-acetyloxy-Δ⁴-pregnene-11β,17α-diol-20-one 6.14 ml of phenyl isocyanate were added at 20° C. to a solution of 23.2 g of the syn and anti isomers of Example 1 in 370 ml of ethyl ether and the mixture was extracted with ethyl acetate. The extracts were washed, dried and filtered and the recovered product was dried to obtain 29 g of a product which was chromatographed over silica gel. Elution with an 8-2 benzene-ethyl acetate mixture yielded 7.4 g of a product with an Rf=0.17 which was chromatographed over silica gel and was empasted with refluxing isopropyl ether to obtain 5.21 g of the anti isomer of 3-(phenylaminocarbonyloxyimino)-9α-fluoro-16α-methyl-21-acetyloxy-Δ⁴-pregnene-11β,17α-diol-20-one melting at 142° ∼ 166° C. and 5.6 g of a product with an Rf=0.11 which was crystallized from ethanol and then isopropanol to obtain 4.15 g of the syn isomer melting at 212° C.

RMN Spectrum (CHCl₃):
anti isomer: 8.33 ppm (NH); 5.92 ppm (ethylenic 4-hydrogen)
RMN Spectrum (CDCl₃):
syn isomer: 8.28 ppm (NH); 6.59 ppm (ethylenic 4-hydrogen)

EXAMPLE 20 syn isomer of 3-(phenylaminocarbonyloxyimino)-9α-fluoro-16α-methyl-Δ⁴-pregnene-11β,17α,21-triol-20-one 5 ml of a N sodium hydroxide solution were added at 0° C. to a suspension of 2.4 g of the syn isomer of Example 9 in 212 ml of ethanol and the mixture was stirred at 0° C. for 10 minutes and was then poured into 1000 ml of ice water. The mixture was gently evaporated under reduced pressure until crystallization started and was then iced and vacuum filtered. The product was washed with water and dried and the raw product was chromatographed over silica gel. Elution with benzene yielded 1.520 g of a product with an Rf=0.18 which was crystallized from methanol to obtain the syn isomer of 3-(phenylaminocarbonyloxyimino)-9α-fluoro-16α-methyl-Δ$^4$-pregnene-11β,17α,21-triol-20-one melting at 254° C. and having a specific rotation of $[α]_D^{20} = +227°$ (c=0.1% in ethanol).

RMN Spectrum (DMSO):

9.67 ppm (NH); 6.45 ppm (ethylenic 4-hydrogen)

EXAMPLE 21 anti isomer of 3-(phenylaminocarbonyloxyimino)-9α-fluoro-16α-methyl-Δ$^4$-pregnene-11β,17α,21-triol-20-one 6.1 ml of a N sodium hydroxide solution were added at 0° C. to a solution of 2.350 g of the anti isomer of Example 9 in 18.8 ml of ethanol and the mixture was stirred at 0° C. for 10 minutes and was diluted with water. The mixture was extracted with ethyl acetate and 2.02 g of product were recovered which was chromatographed over silica gel. Elution with a 9-1 chloroform-acetone mixture yielded 1.83 g of raw product with an Rf=0.23 which was empasted with isopropyl ether, vacuum filtered and dried to obtain the anti isomer of 3-(phenylaminocarbonyloxyimino)-9α-fluoro-16α-methyl-Δ$^4$-pregnene-11β,17α,21-triol-20-one melting at 165° C. and having a specific rotation of $[α]_D^{20} = +135°$ (c=0.1% in ethanol).

RMN Spectrum (CDCl$_3$):

5.98 ppm (ethylenic 4-hydrogen); 8.45 ppm (NH)

EXAMPLE 22

Tablets were prepared containing 5 mg of syn isomer of 3-methoxyimino-9α-fluoro-16α-methyl-Δ$^4$-pregnene-11β,17α-21-triol-20-one or of anti isomer of 3-(phenylaminocarbonyloxyimino)-9α-fluoro-16α-methyl-Δ$^4$-pregnene-11β,17α,21-triol-20-one and sufficient excipient of talc, starch and magnesium stearate for a final weight of 50 mg.

PHARMACOLOGICAL DATA

The antiallergic properties were determined with the compounds of Examples 2,14,16 and 21 and were compared with dexamethasone.

A. Passive cutaneous anaphylaxia (IgE)

The passive cutaneous anaphylaxia test consisted of provoking in rats an antigen-antibody reaction by intraveinous administration of antigen in a cutaneous site which received previously by injection antibodies prepared by injecting an other animal with the same antigen. This reaction is visualized due to a colorant injected at the same time as the antigen. There appears at the point of the injection antibodies a colored spot, proof of the bursting of sensitive cells and of the increase in capillary permeability resulting therefrom. The test was inspired by that of Ovary [J. Immunol., Vol. 81 (1958), p. 355].

The serum containing the antibodies was obtained by combining the serum of male mice weighing 25±1 g immunized 8 days previously by subcutaneous injection at 5 points in the back of a dose of 50 µg of ovalbumin adsorbed on 20 mg of alumina. This serum is standardized by investigation of the greatest dilution which gives a spot with a diameter of about 13 mm in each animal and the antibodies formed under these conditions are IgE.

An adequate dilution of the serum is intradermically injected into male rats weighing about 100 g in a volume of 0.1 ml in the region of the back. 48 hours later, the animals received veinously 0.5 ml of a solution of 0.5% ovalbumin and 1% of Evans blue in an isotonic solution of sodium chloride. 30 minutes after this injection, the rats were bloodlessly killed and the diameter of the blue spot was measured by turning back the skin. Treatments were effected orally on groups of 8 animals 24 and 6 hours before the activating injection and the protective effect was calculated as a percentage with respect to the average spot diameter of the controls and the DA$_{50}$, the dose which reduced the diameter of the spots by 50% as compared to the controls, is reported in Table I.

TABLE I

| Tested Products | DA$_{50}$ in mg/kg |
|---|---|
| anti isomer: Ex. 2 | 2.5 |
| syn isomer: Ex. 2 | 1.4 |
| dexamethasone | 0.3 |

The results of Table I show that the tested compounds were 8 and 4.5 times less active, respectively, than dexamethasone.

B. Anaphylactic shock

The test which was inspired by Nakamura et al [Arzneim, Forsch., Vol. 20 (1970), p. 1033] consisted of administering to the pads of the rear paws of male mice of the Swiss SPF strain weighing about 30 g an injection of 0.05 ml of a suspension of albumin beef serum at 10 mg/ml in Fruend adjuvant. Mortal anaphylactic shock is provoked 8 days after intraveinous injection of 0.3 mg of beef serum albumin in a volume of 0.1 ml. The test products and dexamethasone were orally administered as a suspension in an aqueous dispersion containing 0.25% of carboxymethyl cellulose and 0.20% of polysorbate 80, 24 hours and 3 hours before the activating injection and the DA$_{50}$, the dose that reduced the mortality by 50% as compared to the controls, is reported in Table II.

TABLE II

| Tested Products | DA$_{50}$ in mg/kg |
|---|---|
| ex 2: anti isomer | 1.8 |
| ex 2: syn isomer | 1.2 |
| ex 14: syn isomer | 1.4 |
| ex 24: anti isomer | 1.5 |
| ex 16: anti isomer | 0.8 |
| ex 16: anti isomer | 1.2 |
| ex 21: | 0.7 |
| Dexamethasone | 1.7 |

The results of Table II show that the tested compounds have an activity comparable to that of dexamethasone.

C. Anti-inflammatory Activity

The test used is the classic granuloma test of Meier et al [Experientia, Vol. 6 (1950), p. 469] in which female rats of the conventional Wistar strain weighing 100 to 110 g received implantation of 2 cotton pellets weighing 10 mg each in the thorax skin. Oral treatment started after the implantation for 2 days with 2 administrations per day. 16 hours after the last administration or on the 3rd day, the animals were killed and the pellets encircled with the tissue of the formed granuloma were weighed in the fresh state and then after 18 hours at 60° C. The weight of the granuloma was determined by substracting the initial weight of the cotton and the $DA_{50}$, the dose which inhibited by 50% the granuloma, is reported in Table III.

TABLE III

| Tested Products | $DA_{50}$ in mg/kg |
|---|---|
| ex 2: syn isomer | 2 |
| ex 2: anti isomer | 2.6 |
| ex 14: syn isomer | 3.5 |
| ex 16: syn isomer | 5 |
| ex 21: | 2.5 |
| Dexamethasone | 0.05 |

The results of Table III show that the compounds of the invention are 40 to 100 times less effective as anti-inflammatory agents than dexamethasone.

Various modifications of the products and methods of the invention may be made without departing from the spirit or scope thereof and it is to be understood that the invention is to be limited only as defined in the appended claims.

We claim:

1. A compound of the formula

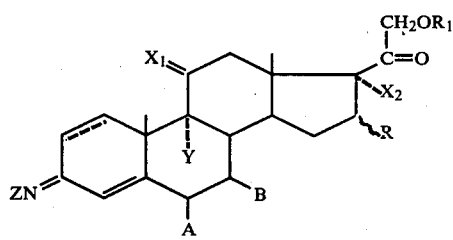

wherein $X_1$ is selected from the group consisting of =O and

Y is selected from the group consisting of hydrogen and halogen, $R_1$ is selected from the group consisting of hydrogen and acyl of an organic carboxylic acid of 1 to 18 carbon atoms, $X_2$ is selected from the group consisting of hydrogen and —OH, R in the 16α- or β-position is selected from the group consisting of hydrogen, —OH and methyl, Z is selected from the group consisting of (1) —OH, (2) alkoxy of 1 to 12 carbon atoms, (3) cycloalkoxy of 3 to 12 carbon atoms, (4) acyloxy of an organic carboxylic acid of 1 to 18 carbon atoms, (5)

wherein W is a hydrocarbon of 1 to 12 carbon atoms, (6)

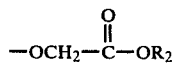

wherein $R_2$ is hydrogen or alkyl of 1 to 12 carbon atoms, (7)

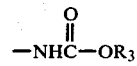

where $R_3$ is a hydrocarbon of 1 to 12 carbon atoms and (8)

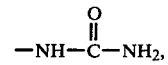

the dotted line in the A ring indicates the optional presence of a double bond in the 1(2)-position and A and B are both hydrogen or A is methyl, chlorine or fluorine while B is hydrogen or A and B may form a double bond in the 6(7)-position with the proviso that if the A ring has a 1(2) double bond, A is hydrogen or fluorine, B is hydrogen, Y is hydrogen or fluorine, $X_2$ is hydrogen or —OH, R is methyl and Z is not —OH.

2. A compound of claim 1 wherein Z is other than —OH and alkoxy, $X_2$ is —OH, R and Y are hydrogen and A and B are hydrogen.

3. A compound of claim 1 wherein the A ring is saturated in the 1(2)-position.

4. A compound of claim 1 wherein A and B are hydrogen.

5. A compound of claim 1 wherein $X_1$ is

6. A compound of claim 1 wherein $X_2$ is selected from the group consisting of hydrogen and —OH.

7. A compound of claim 1 wherein R is 16α-methyl.

8. A compound of claim 1 wherein Y is 9α-fluoro.

9. A compound of claim 1 wherein $R_1$ is selected from the group consisting of hydrogen and acyl of an organic carboxylic acid of 1 to 18 carbon atoms.

10. A compound of claim 1 selected from the group consisting of syn isomer and the anti isomer of 3-methoxyimino-9α-fluoro-16α-methyl-Δ⁴-pregnene-11β,17α,21-triol-20-one.

11. An anti allergic composition comprising an antiallergically effective amount of at least one compound of claim 1 and an inert pharmaceutical carrier.

12. A composition of claim 11 wherein the compound is selected from the group consisting of the syn isomer and the anti isomer of 3-methoxyimino-9α-fluoro-16α-methyl-Δ⁴-pregnene-11β,17α,21-triol-20-one.

13. A method of treating allergic conditions in warm-blooded animals comprising administering to warm-blooded animals an antiallergically effective amount of at least one compound of claim 1.

14. The method of claim 13 wherein the compound is orally administered.

15. A method of claim 13 wherein Z is other than —OH and alkoxy, $X_2$ is —OH, R and Y are hydrogen and A and B are hydrogen.

16. A method of claim 13 wherein the A ring is saturated in the 1(2)-position.

17. A method of claim 13 wherein A and B are hydrogen.

18. A method of claim 13 wherein $X_1$ is

19. A method of claim 13 wherein X₂ is selected from the group consisting of hydrogen and —OH.

20. A method of claim 13 wherein R is 16α-methyl.

21. A method of claim 13 wherein Y is 9α-fluoro.

22. A method of claim 13 wherein R₁ is selected from the group consisting of hydrogen and acyl of an organic carboxylic acid of 1 to 18 carbon atoms.

23. A method of claim 13 wherein the compound is selected from the group consisting of the syn isomer and the anti isomer of 3-methoxyimino-9α-fluoro-16α-methyl-Δ⁴-pregnene-11β,17α,21-triol-20-one.

* * * * *